(12) United States Patent
Lucht

(10) Patent No.: US 12,310,932 B2
(45) Date of Patent: May 27, 2025

(54) SUBLINGUAL PHENTERMINE SPRAY COMPOSITIONS AND DAY-NIGHT APPETITE SUPPRESSION AND WEIGHT LOSS REGIMEN USING SAME

(71) Applicant: Red Mountain Med Spa, LLC, Scottsdale, AZ (US)

(72) Inventor: Austin Lucht, Scottsdale, AZ (US)

(73) Assignee: Red Mountain Med Spa, LLC, Scottsdale, AZ (US)

(*) Notice: Subject to any disclaimer, the term of this patent is extended or adjusted under 35 U.S.C. 154(b) by 0 days.

(21) Appl. No.: 18/392,193

(22) Filed: Dec. 21, 2023

(65) Prior Publication Data
US 2024/0277634 A1    Aug. 22, 2024

Related U.S. Application Data

(62) Division of application No. 18/171,822, filed on Feb. 21, 2023.

(51) Int. Cl.
| | | |
|---|---|---|
| *A61K 31/137* | (2006.01) | |
| *A61K 9/00* | (2006.01) | |
| *A61K 31/4045* | (2006.01) | |
| *A61K 47/10* | (2017.01) | |
| *A61K 47/14* | (2017.01) | |
| *A61K 47/26* | (2006.01) | |

(52) U.S. Cl.
CPC ............ *A61K 31/137* (2013.01); *A61K 9/006* (2013.01); *A61K 31/4045* (2013.01); *A61K 47/10* (2013.01); *A61K 47/14* (2013.01); *A61K 47/26* (2013.01)

(58) Field of Classification Search
CPC .. A61K 31/137; A61K 9/006; A61K 31/4045; A61K 47/10; A61K 47/14; A61K 47/26; A61K 9/08; A61K 47/44
See application file for complete search history.

(56) References Cited

U.S. PATENT DOCUMENTS

| | | | |
|---|---|---|---|
| 5,019,594 | A | 5/1991 | Wurtman |
| 5,534,272 | A | 7/1996 | Bernstein |
| 5,543,405 | A | 8/1996 | Keown |
| 2003/0095925 | A1 | 5/2003 | Dugger, III |
| 2004/0044303 | A1 | 3/2004 | Katz |
| 2004/0146469 | A1 | 7/2004 | Reed et al. |
| 2004/0204472 | A1 | 10/2004 | Briggs |
| 2012/0310211 | A1 | 12/2012 | Du Toit et al. |
| 2021/0275536 | A1 | 9/2021 | Bentz |
| 2022/0000763 | A1 | 1/2022 | Dely |

FOREIGN PATENT DOCUMENTS

| | | |
|---|---|---|
| CA | 2174422 | 4/1995 |
| CN | 101283804 | 10/2008 |
| CN | 104736147 | 5/2015 |
| WO | 0025806 | 5/2000 |

OTHER PUBLICATIONS

USPTO; Non-Final Office Action dated Jan. 31, 2024 in U.S. Appl. No. 18/171,822.
Reddy et al. "A Review on Bioadhesive Buccal Drug Delivery Systems: Current Status of Formulation and Evaluation Methods." DARU Journal of Pharmaceutical Sciences, vol. 19, No. 6, 2011, pp. 385-403. (Year: 2011).
CIPO, Examination Report dated Feb. 20, 2024 in Canadian Application No. 3175950.
Amandean Nnatural Products, "Why Weight Watcher Fans are Using Marine Collagen As Part of Their Daily Nutrition?", https://www.amandean.com/blogs/news/marine-collagen-as-the-best-protein-to-pair-with-your-weight-watchers-program, Jan. 17, 2019, 11 pages.
Hans Bundgaard, "Design of Prodrugs", 1985 Elsevier Amsterdam, New York—Oxford, (Year: 1985), ISBN 0-444-80675-X, 94 pages.
Silverman, "Prodrugs and Drug Delivery Systems, The Organic Chemistry of Drug Design and Drug Action", pp. 352-399, 1992, Chapter 8, (Year: 1992), 25 pages.
Wolff, Burger's, "Principles and Practice", Medicinal Chemistry and Drug Discovery, 5th Edition, vol. I, pp. 975-977, 1995 (Year: 1995).
Banker et al., Prod rugs, "Modern Pharmaceutics", Third Edition and Expanded, pp. 451 and 596 (1996) (Year: 1996).
USPTO, Restriction/Election Requirement dated Jun. 25, 2021 in U.S. Appl. No. 16/808,084.
USPTO, Non-Final Office Action dated Aug. 18, 2021 in U.S. Appl. No. 16/808,084.
USPTO, Final Office Action dated Nov. 30, 2021 in U.S. Appl. No. 16/808,084.
USPTO, Advisory Action dated Dec. 29, 2021 in U.S. Appl. No. 16/808,084.
CIPO, Examination Report dated Jul. 12, 2021 in CA Application No. 3,074,541.
CIPO, Examination Report dated Dec. 13, 2021 in CA Application No. 3,074,541.

(Continued)

*Primary Examiner* — Valerie Rodriguez-Garcia
*Assistant Examiner* — Kyle Nottingham
(74) *Attorney, Agent, or Firm* — SNELL & WILMER L.L.P.

(57) ABSTRACT

A sublingual phentermine spray composition for daytime use comprises phentermine in a pharmaceutically-acceptable carrier and a sublingual phentermine spray composition for nighttime use comprises phentermine and a sleep aid in a pharmaceutically-acceptable carrier. Sublingual administration of sublingual phentermine spray compositions in accordance with the present disclosure provides an alternative to oral administration, avoiding such side effects as daytime drowsiness and intestinal disturbances. Nighttime use compositions comprising a sleep aid such as melatonin help manage the usual insomnia experienced when using phentermine. These compositions find use in suppressing appetite, for losing weight, and for maintaining a desired personal appearance.

7 Claims, No Drawings

(56) References Cited

OTHER PUBLICATIONS

Gavilanes, G., "Can You Use Collagen For Weight Loss?", https://www.vitalproteins.com/blogs/stay-vital/collagen-for-weight-loss Jan. 21, 2019 (Jan. 21, 2019); 4 pages.
Lynn, L., "Does Taking A Collagen Supplement Hurt Your Weight Loss?", https://lynfit.com/blogs/news/does-taking-a-collagen-supplement-hurt-your-weight-loss Mar. 18, 2019 (Mar. 18, 2019); 6 pages.
USPTO, Notice of Allowance dated Mar. 8, 2022 in U.S. Appl. No. 16/808,084.
USPTO, Corrected Notice of Allowance dated Mar. 22, 2022 in U.S. Appl. No. 16/808,084.
Cipo, Examination Report dated Jul. 14, 2022 in Canadian Application No. 3,074,541.
CIPO, Notice of Allowance dated Mar. 13, 2023 in Canadian Application No. 3,074,541.
USPTO, Restriction/Election Requirement dated Jun. 23, 2023 in U.S. Appl. No. 17/733,690.
USPTO, Non-Final Office Action dated Aug. 7, 2023 in U.S. Appl. No. 17/733,690.
USPTO, Restriction/Election Requirement dated Sep. 26, 2023 in U.S. Appl. No. 18/171,822.
Kinman, Tricia ."About Sublingual and Buccal Medication Administration." Healthline, Jun. 6, 2017, https://www.healthline.com/health/sublingual-and-buccal-medication-administration. (Year: 2017), pp. 1-2.
Gonzales, Sarah. "Combining Phentermine with Other Supplements." PhenOnline, Oct. 5, 2022, https://phenonline.com/blog/combining-phentermine-with-other-supplements/. (Year: 2022), pp. 1-6.
drugs.com. "Nitroglycerin Lingual Spray: Package Insert." https://www.drugs.com/pro/nitroglycerin-lingual-spray.html. Last updated Feb. 5, 2023 (Year: 2023), 20 pages.
Evolvent. "Table of Viscosities"; https://oilviscositychart.com/learn/viscosity-list.php. Accessed Oct. 16, 2023. (Year: 2023), pp. 1-17.
NHR Organic Oils. "Certificate of Analysis Sheet: Organic MCT oil"; https://www.nhrorganicoils.com/uploads/certs/MCT%20CofA%20110718-17.pdf. Accessed Oct. 16, 2023 (Year: 2018), 1 page.
USPTO, Non-Final Office Action dated Oct. 23, 2023 in U.S. Appl. No. 18/171,822.
USPTO; Notice of Allowance dated Nov. 17, 2023 in U.S. Appl. No. 17/733,690.
USPTO; Restriction Requirement dated Aug. 27, 2024 in U.S. Appl. No. 18/171,822.
USPTO; Restriction Requirement dated Jul. 16, 2024 in U.S. Appl. No. 18/501,814.
USPTO; Final Office Action dated May 13, 2024 in U.S. Appl. No. 18/171,822.
Hassan et al. "Chemical Permeation Enhancers for Transbuccal Drug Delivery." Expert Opinion on Drug Delivery, vol. 7, No. 1, Jan. 2010, p. 97-112. DOI.org, https://doi.org/10.1517/17425240903338758.
National Center for Biotechnology Information. "PubChem Compound Summary for CID 4771, Phentermine" PubChem, 2005, https://pubchem.ncbi.nlm.nih.gov/compound/Phentermine. Accessed Jul. 25, 2024. 106 pages.
USPTO; Advisory Action dated Jul. 30, 2024 in U.S. Appl. No. 18/171,822.
USPTO; Non-Final Office Action dated Oct. 22, 2024 in U.S. Appl. No. 18/501,814.
USPTO; Non-Final Office Action dated Nov. 4, 2024 in U.S. Appl. No. 18/171,822.
Aravindhanthan et al. "Sublingual spray: a new technology oriented formulation with multiple benefits." International Journal of Research in Pharmaceutical Sciences, vol. 10, No. 4, Oct. 2019, https://doi.org/10.26452/ijrps.v10i4. 1567, pp. 2875-2885.
USPTO; Notice of Allowance dated Feb. 5, 2025 in U.S. Appl. No. 18/501,814.

SUBLINGUAL PHENTERMINE SPRAY COMPOSITIONS AND DAY-NIGHT APPETITE SUPPRESSION AND WEIGHT LOSS REGIMEN USING SAME

CROSS REFERENCE TO A RELATED APPLICATION

This Application is a divisional of U.S. Non-Provisional application Ser. No. 18/171,822, filed Feb. 21, 2023. The contents of which are incorporated herein by reference in its entirety as if set forth verbatim.

FIELD

This disclosure generally relates to pharmaceutical compositions used for weight loss, and more specifically, to sublingually administered weight loss compositions and day and night regimens for using same.

BACKGROUND

Individuals from industrialized countries are often increasingly obsessed by health and beauty. These individuals typically help fuel a multi-billion dollar market for over the counter (OTC) diet products, medically assisted weight loss (e.g., prescription drugs and bariatric surgery, cosmetic surgery and cosmetics) and anti-aging treatments. Some individuals may find difficulty maintaining and coordinating both proper diet and exercise regimen and often turn to pharmaceutically active formulations and programs promoting rapid weight loss and body sculpting.

One weight loss drug used for decades in the treatment of obesity is phentermine. Although approved in the U.S. as far back as 1959, administration of phentermine is still oral, and the associated discomfort and side effects from oral administration have never been addressed. A full dose of phentermine (37.5 mg phentermine-HCl, orally ingested once daily) causes gastrointestinal side effects including nausea, vomiting, cramps, diarrhea and constipation. Administration of this bolus amount in a single dose used for sufficient gastrointestinal absorption exacerbates these gastric issues, and even a half tablet twice daily (recommended for some patients) still may cause these issues. The discomfort encountered when taking orally administered phentermine typically contributes to waning patient compliance.

Other issues arise from oral administration of phentermine. For example, the drug is known to cause insomnia, so patients are faced with gastrointestinal issues throughout the day and insomnia at night. Ironically, splitting a tablet into two doses merely delays administration of the second half closer to bedtime, further exacerbating insomnia.

In view of these and other problems associated with phentermine tablets for oral administration, new physical forms and dosage regimens are needed so that patients having been prescribed phentermine can remain compliant and stay the course of their weight loss program.

SUMMARY

It has now been surprisingly discovered that transmucosal administration of phentermine across sublingual mucosa provides a viable alternative to oral administration. Further, it has been remarkably discovered that the active amount of phentermine administered daily can be dramatically reduced from the usual 37.5 mg phentermine-HCl required for oral dosing. Sublingual administration of phentermine provides an administrative route for phentermine that avoids the inevitable gastric issues and drowsiness seen with oral administration. Addition of a sleep aid such as melatonin to a sublingual phentermine spray composition provides a spray for nighttime use that mitigates the typical insomnia seen with orally administered phentermine.

In various embodiments, sublingual phentermine spray compositions are described. In certain examples, a sublingual phentermine spray composition is formulated for daytime use. In other examples, a sublingual phentermine spray composition is formulated for nighttime use.

In various embodiments, a weight loss regimen comprises daytime sublingual administration of a sublingual phentermine spray composition formulated for daytime use and nighttime sublingual administration of a sublingual phentermine spray composition formulated for nighttime use.

In various embodiments, a weight loss kit comprises a sublingual phentermine spray composition formulated for daytime use, a sublingual phentermine spray composition formulated for nighttime use, and a day-night weight loss regimen in the form of usage instructions provided with the kit.

In various embodiments, a method of appetite suppression or weight loss comprises daytime sublingual administration of a sublingual phentermine spray composition formulated for daytime use to an individual in need thereof, and nighttime sublingual administration of a sublingual phentermine spray composition formulated for nighttime use to the individual in need thereof.

In various embodiments of the method, the individual in need thereof is diagnosed overweight and/or obese.

In various embodiments, a sublingual phentermine spray composition comprises phentermine or a phentermine salt; and a carrier; wherein the sublingual phentermine spray composition is a liquid having a viscosity of about 1 cp to about 100 cp.

In various embodiments, the phentermine salt comprises phentermine-HCl, present at from about 4.5 wt. % to about 10 wt. %, based on the total weight of the composition.

In various embodiments, the carrier comprises an oil, a surfactant, a solvent, and, optionally, any one of a salt, flavoring agent, sweetener, masking agent, and preservative.

In various embodiments, the oil comprises medium-chain triglycerides (MCT).

In various embodiments, the surfactant comprises polysorbate 80.

In various embodiments, the solvent comprises ethanol.

In various embodiments, the sublingual phentermine spray composition further comprises a sleep aid.

In various embodiments, the sleep aid comprises melatonin, present at from about 0.75 wt. % to about 1.25 wt. %, based on the total weight of the composition.

In various embodiments, a method for suppressing appetite or for promoting weight loss in an individual in need thereof comprises:
sublingually administering to the individual a therapeutically effective amount of a combination of a sublingual phentermine spray composition for daytime use and a sublingual phentermine spray composition for nighttime use;
wherein the sublingual phentermine spray composition for daytime use comprises from about 7.5 wt. % to about 10 wt. % phentermine-HCl, based on the total weight of the sublingual phentermine spray composition for daytime use; and a carrier;
wherein the sublingual phentermine spray composition for nighttime use comprises from about 4.5 wt. % to about 7.5 wt. % phentermine-HCl, based on the total weight of the sublingual phentermine spray composition for nighttime use; from about 0.75 wt. % to about 1.25 wt. % of a sleep aid, based on the total weight of the sublingual phentermine spray composition for nighttime use; and a carrier;

wherein each of the sublingual phentermine spray composition for daytime use and the sublingual phentermine spray composition for nighttime use is a liquid having a viscosity of from about 1 cp to about 100 cp; and wherein the sublingual phentermine spray composition for daytime use is sublingually administered to the individual in the daytime hours and wherein the sublingual phentermine spray composition for nighttime use is sublingually administered to the individual at night before bedtime.

In various embodiments, the sleep aid is melatonin.

In various embodiments, the therapeutically effective amount is an amount sufficient of the combination of sublingual phentermine spray composition for daytime use and the sublingual phentermine spray composition for nighttime use to deliver a total of from about 12.5 mg to about 37.5 mg active phentermine and from about 1 mg to about 3 mg melatonin daily.

In various embodiments, the total of from about 12.5 mg to about 37.5 mg active phentermine and from about 1 mg to about 3 mg melatonin daily is obtained from one to three spray doses daily of the sublingual phentermine spray composition for daytime use and from one to three spray doses daily of the sublingual phentermine spray composition for nighttime use.

In various embodiments, the individual in need thereof is diagnosed overweight or obese.

In various embodiments, a kit for use in suppressing appetite or for promoting weight loss in an individual in need thereof comprises:

a first non-aerosol pump spray bottle equipped with an actuator and containing a volume of a sublingual phentermine spray composition for daytime use, the sublingual phentermine spray composition for daytime use comprising about 7.5 wt. % to about 10 wt. % phentermine-HCl in a carrier comprising an oil, a surfactant, a solvent, and optional excipients;

a second non-aerosol pump spray bottle equipped with an actuator and containing a volume of a sublingual phentermine spray composition for nighttime use, the sublingual phentermine spray composition for nighttime use comprising about 4.5 wt. % to about 7.5 wt. % phentermine-HCl and about 0.75 wt. % to about 1.25 wt. % melatonin in the carrier comprising the oil, the surfactant, the solvent, and the optional excipients;

a package enclosing the first and second non-aerosol pump spray bottles; and instructions for use of the kit, said instructions provided on or in the package, or provided as remotely accessible information.

In various embodiments, the oil comprises medium-chain triglycerides (MCT).

In various embodiments, the surfactant comprises polysorbate 80.

In various embodiments, the solvent comprises ethanol.

In various embodiments, the instructions inform the individual in need thereof to sublingually self-administer from one to three non-aerosol spray actuations of the sublingual phentermine spray composition for daytime use from the first non-aerosol pump spray bottle daily during the waking hours and to sublingually self-administer from one to three non-aerosol spray actuations of the sublingual phentermine spray composition for nighttime use from the second non-aerosol pump spray bottle daily prior to bedtime.

In various embodiments, each non-aerosol spray actuation from the first non-aerosol pump spray bottle and each non-aerosol spray actuation from the second non-aerosol pump spray bottle measure from about 0.12 mL to about 0.14 mL in volume.

In various embodiments, each 0.12 mL non-aerosol spray actuation from the first non-aerosol pump spray bottle comprises about 7.5 mg active phentermine and wherein each 0.12 mL non-aerosol spray actuation from the second non-aerosol pump spray bottle comprises about 5 mg active phentermine and about 1 mg melatonin.

DETAILED DESCRIPTION

The detailed description of exemplary embodiments refers to the accompanying drawings, which show exemplary embodiments by way of illustration and best mode. While these exemplary embodiments are described in enough detail to enable those skilled in the art to practice the invention, other embodiments may be realized, and logical, chemical, and mechanical changes may be made without departing from the spirit and scope of the inventions. Thus, the detailed description is presented for purposes of illustration only and not of limitation. For example, unless otherwise noted, the steps recited in any of the method or process descriptions may be executed in any order and are not necessarily limited to the order presented. Furthermore, any reference to singular includes plural embodiments, and any reference to more than one component or step may include a singular embodiment or step. Also, any reference to attached, fixed, connected or the like may include permanent, removable, temporary, partial, full and/or any other possible attachment option. Additionally, any reference to without contact (or similar phrases) may also include reduced contact or minimal contact.

Sublingual phentermine spray compositions (specially formulated in both a daytime composition and a nighttime composition) are described, along with kits comprising both versions of sublingual phentermine spray compositions, dosage regimens, and methods of appetite suppression and weight loss using the compositions or the kit. In various embodiments, sublingual phentermine spray compositions in accordance with the present disclosure are optimized for transmucosal permeation across sublingual mucosa, allowing for a substantial reduction in the actives amount necessary per day.

Definitions

As used herein, the name "phentermine" is the trivial chemical name for α-methylamphetamine or, in IUPAC nomenclature, 2-methyl-1-phenylpropan-2-amine. Various salt forms of phentermine, such as phentermine-HCl (i.e., $C_{10}H_{16}N^+X^-$, wherein X=Cl), find use in the compositions herein, although it is important to note that the scope of the present disclosure is not limited by the choice of the counterion $X^-$ associated with protonated phentermine $C_{10}H_{16}N^+$.

As used herein, the terms "oil" refers to pharmaceutically acceptable diluents that help to solubilize, emulsify or disperse a drug active, such as phentermine-HCl, into a physical form and/or volume more easily and effectively dosed. In some instances, an oil increases bioavailability of a drug active such as by promoting sublingual absorption. An oil herein can be considered an excipient in a pharmaceutical composition and may also be characterized as a vehicle or a carrier by itself, or a component of a pharmaceutically acceptable carrier. Examples of oils for use herein include, but are not limited to, natural, partially hydrogenated, or fully hydrogenated vegetable oils such as soybean oil, olive oil, sesame oil, palm oil, coconut oil, and the like. Oils may also be fractionated cuts of fatty acids, fatty acid mixtures, mono-, di-, or triglycerides of fatty acids, wherein the fatty acids and/or glycerides may have a particular chain length distribution (e.g., short-, medium-, or long-chain fatty acids). Of particular use herein are "medium-chain triglycerides" (or "MCT's"), which refers to the glycerin triesters of fatty acids having from about 6 to about 12 carbon atoms, such as caprylic acid, caproic acid, lauric acid, and/or capric acid in any combination, (i.e., $C_6$-$C_{12}$ fatty acid triglycerides). In various examples, medium-chain triglycerides can be obtained by fractionating palm kernel oil and coconut oil. Medium-chain triglycerides, USP/NF, CAS No. 73398-61-5, for use in the compositions herein is available, for example, from Specialized Rx Products, LLC, Circle Pines, MN. Also of use herein is Organic MCT Oil-Fractionated Coconut Oil (caprylic/capric triglyceride), CAS Nos. 73398-61-5 and 65381-09-1, having a specific gravity of about 0.930-0.960 g/mL (typically on average, 0.951 g/mL).

As used herein, the term "carrier" refers to a mixture of compounds other than drug actives present in a pharmaceutical composition. As mentioned, a carrier may comprise an oil, and thus the carrier with an oil has a functional role of solubilizing, emulsifying or dispersing a drug active. In some examples, a carrier is necessary to at least provide a convenient dosage volume for a drug active since without a carrier it would be impractical for patients to handle and self-administer milligram quantities of a drug active. Further, a carrier may be necessary to provide a drug active in a certain physical form for dosage, such as a liquid form, and/or to promote absorption and bioavailability. In other words, a carrier might be used to dissolve an otherwise solid drug active such that the final composition for use is a liquid. In the context of the sublingual phentermine spray compositions herein, the carrier in the composition enables a liquid dosage form along with sufficient volume so that a measurable spray or "spritz" from a suitable dispenser provides a recommended sublingual dosage of phentermine.

For the sublingual phentermine spray compositions herein, a carrier for the phentermine active may comprise any combination of oils, surfactants, dispersants, emulsifiers, solubilizers, salts, acidic agents, alkaline agents, pH buffers, solvents (e.g., for example, water, ethanol and/or PEG), permeation/absorption enhancers, coloring agents, flavoring agents, flavor masking agents, sweeteners, and preservatives.

As used herein, the term "surfactant" takes on its ordinary meaning in chemistry but recognizing that many surfactants act more as emulsifying or solubilizing agents rather than surface active agents. Surfactants for use in carrier mixtures for phentermine herein may be anionic, cationic, nonionic, or amphoteric. Preferred nonionic surfactants include sugar esters, such as, for example, sorbitan fatty acid esters sold under the trade name Span®, and polyethoxylated (POE) sorbitan fatty acid esters sold under the trade name Tween®. Of particular interest herein is polysorbate 80, $C_{64}H_{124}O_{26}$ (available as Tween® 80) which is a sorbitan monooleate ethoxylated with a total of about 20 (POE) units. Other polysorbates, such as lauryl esters rather than oleic esters, other (POE) levels, also find use herein. Polysorbates and sorbitan esters suitable for use as emulsifiers in the carrier systems herein are available, for example, from BASF Pharma. Florham Park, NJ.

As used herein, the term "solvent" takes on its ordinary meaning in formulation chemistry, recognizing that for purposes herein this term includes lower molecular weight glycols such as propylene glycol and polyethylene glycols (PEGs) in addition to the more familiar water and ethanol. PEGs are solubilizers, forming solvent systems when dissolved in water and/or ethanol. Any combination of solvents such as water, ethanol, propylene glycol, and PEG may be used herein to dissolve phentermine or a phentermine salt into a dispensable liquid. For a review of the use of PEG in pharmaceutical compositions, see A. D'souza, et al., "Polyethylene glycol (PEG): a versatile polymer for pharmaceutical applications." *Expert Opinion on Drug Delivery,* 13(9), 1257-1275 (2016).

As used herein, the term "sleep aid" refers to a chemical ingredient or botanical compound or botanical mixture capable of promoting sleep in an individual. In preferred embodiments herein, a sublingual phentermine spray composition for nighttime use further includes a sleep aid. In various examples, the sleep aid is melatonin, valerian root extract, L-γ-glutamylethylamide, lavender oil, or γ-aminobutyric acid (GABA), or other naturally occurring animal, plant or fungal substance. In other examples, a sleep aid for use in a sublingual phentermine spray composition for nighttime use comprises a drug active, such as diphenhydramine or doxylamine.

As used herein, the term "composition" takes on the ordinary meaning in formulation chemistry as a combination of ingredients. Simply written, a pharmaceutical composition may comprise a drug active and a suitable carrier. In various embodiments, a composition is designed to adopt a particular physical form, or at least be amenable to physical change into a desired physical form, which may be the dosage form for a particular treatment regimen. Typically, a composition is made homogeneous by mixing or blending, although not all liquid compositions are colorless and/or transparent and not all powder compositions are white and/or perfectly granular. Compositions comprising an emulsion, dispersion or suspension may be homogeneous because the droplets or particles are too small to diffract light and are evenly spread in a carrier. So, for example, a composition herein may be in the form of a thin liquid (having a viscosity at or near that of water), a viscous liquid (having a liquid of viscosity greater than water), a paste, or a gel. In various embodiments, a composition herein comprises a liquid mixture suitable for sublingual administration as a bolus or as a spray from a spray dispenser.

Ingredients for a composition herein are generally shown "as added," meaning there is a possibility for one or more chemical reactions between ingredients once the ingredients are mixed together, such as into a common carrier. One skilled in the art of formulation chemistry can recognize whether ingredients might react in a mixture. These reactions can include neutralization (e.g., between acid and alkali ingredients), mixed micelle formation (mixed surfactants in liquid systems) or other encapsulation phenomena, hydrolysis, and so forth. In various embodiments, ingredients in a composition are listed in "weight percent." (i.e., "wt. %"), based on the total weight of the composition. For example, 100 milligrams of a composition comprising 40 mg A and 60 mg B may be recited as "40) wt. % A and 60 wt. % B, based on the total weight of the composition." which necessarily totals to "100 wt. %." The actual weight amounts. (e.g., milligrams or grams) generally refers to amounts added for a particular batch size. (e.g., a batch size of powder usable to fill 100) capsules).

As used herein, the term "dosage form" takes on its ordinary meaning in the pharmaceutical arts as the physical form of a composition designed for a particular administration route. For sublingual phentermine compositions herein, the dosage form is preferably a liquid, although the liquid dosage form need not be "water thin" (1 cp) as some viscosity (up to about 100 cp) is tolerable in pump sprayers considering fluids are likely to shear in a spray nozzle. The dosage form herein should be deliverable from a throat/mouth spray bottle, such as a 2-60 mL pump spray bottle available from ULINE or U.S. Plastic Corporation.

As used herein, the terms "subject," or "individual," or the phrases "a subject in need thereof." or "an individual in need thereof," refers to any human or non-human animal requiring or desirous of a pharmacological change. For example, a subject in need thereof may be a human patient clinically diagnosed with obesity, an eating disorder, or health issues relating to poor BMI, fat along the waistline, diet in general, or lack of exercise. In various embodiments, the subject in need thereof is a person desirous of a reduced appetite such that they can lose weight and/or improve health. Most importantly, a subject in need thereof can be any human in good health, but desirous of maintaining good health. In other words, the subject in need thereof may be desirous of a prophylactic regimen, like taking daily vitamins to prevent disease. The subject in need thereof may have the outward appearance of a person of average weight for their age, height and gender, but desirous of maintaining that weight, and thus desirous of curbing appetite in general.

As used herein, the term "treatment" of a subject (e.g., a human in need thereof) is any type of intervention used in an attempt to alter the natural course of the subject. Treatment includes, but is not limited to, administration of a sublingual phentermine spray composition in accordance with the present disclosure and may be performed either prophylactically or subsequent to the initiation of a pathologic event or diagnosis of a physical issue, such as obesity. Also included are "prophylactic" treatments, which can be directed to reducing the rate of progression of obesity or condition being treated, delaying the onset of weight or condition, or reducing the severity of its onset. "Treatment" or "prophylaxis" does not necessarily indicate complete eradication, cure, or prevention of a disease or condition, or associated symptoms thereof. Treatment may also be entirely for cosmetic reasons, such as where an individual looks fit and has not received any diagnosis of a weight issue or a need for weight loss, but for whom maintaining a slim figure is believed desirous for some personal reason.

As used herein, the term "therapeutically effective amount" refers to a minimum dosage of a composition in accordance with the present disclosure that provides a desired effect. Therefore, a therapeutically effective amount varies by subject, such as the physical condition of the individual and the need for medical intervention, dosage form, concentration of phentermine active in the composition, and the ultimate results desired. For example, a therapeutically effective amount of a sublingual spray disclosed herein to treat an overweight individual, such as by suppressing the individual's appetite, might be on the order of one (1) sublingual spray of a daytime composition daily, providing a total of about 7.5 mg active phentermine, and/or one (1) sublingual spray of a nighttime composition in the evening, providing about 5 mg active phentermine along with a sleep aid, each spray measuring about 0.12 mL to about 0.14 mL of the composition and each spray of daytime composition delivering about 7.5 mg active phentermine and each spray of nighttime composition delivering about 5 mg active phentermine. In other examples, a therapeutically effective amount of a sublingual spray disclosed herein to treat a morbidly obese individual plagued by constant hunger cravings might be on the order of three (3) sublingual sprays of a daytime composition daily, providing a total of about 22.5 mg active phentermine, and/or three (3) sublingual sprays of a nighttime composition in the evening, providing about 15 mg active phentermine along with a sleep aid, each spray measuring about 0.12 mL to about 0.14 mL of the composition and each spray of daytime composition delivering about 7.5 mg active phentermine and each spray of nighttime composition delivering about 5 mg active phentermine. Dosage regimens to treat overweight or medically obese individuals may vary depending on the eating habits of the individual, such as if the individual experiences night cravings or breakthrough hunger.

As used herein, the term "prophylactically effective amount" refers to a minimum dosage of a composition in accordance with the present disclosure that maintains an individual's present health status when taken regularly, such as an individual's current body weight and/or BMI. In various examples, an individual in need thereof may be an individual desirous of maintaining a healthy appearance. A prophylactically effective amount varies by subject, dosage form, concentration of phentermine active in the composition, and the habits and cravings of the individual. For example, a prophylactically effective amount of a sublingual spray disclosed herein to suppress appetite cravings and help an individual maintain their current weight, BMI and/or overall health or appearance might be on the order of one (1) sublingual spray of a daytime composition daily, providing a total of about 7.5 mg active phentermine, and/or one (1) sublingual spray of a nighttime composition in the evening, providing about 5 mg active phentermine along with a sleep aid, each spray measuring about 0.12 mL to about 0.14 mL of the composition and each spray of daytime composition delivering about 7.5 mg active phentermine and each spray of nighttime composition delivering about 5 mg active phentermine.

As used herein, the term "modulate" includes to "increase" or "decrease" one or more quantifiable parameters, optionally by a defined and/or statistically significant amount. By "increase" or "increasing." "enhance" or "enhancing." or "stimulate" or "stimulating." refers generally to the ability of one or more sublingual phentermine spray compositions in accordance with the present disclosure to produce or cause a greater physiological response (i.e., downstream effects) in a cell or in a subject relative to the response caused by either no phentermine composition or a control compound. Relevant physiological or cellular responses (in vivo or in vitro) upon administration of a sublingual phentermine spray composition will be apparent to persons skilled in the art. An "increased" or "enhanced" amount is typically a "statistically significant" amount, and may include an increase that is 1.1, 1.2, 2, 3, 4, 5, 6, 7, 8, 9, 10, 15, 20, 30, 40, 50 or more times (e.g., 500, 1000 times), including all integers and decimal points in between and above 1 (e.g., 1.5, 1.6, 1.7, 1.8), the amount produced by no sublingual phentermine spray composition (the absence of a bioactive agent) or a control compound. The term "reduce" or "inhibit" may relate generally to the ability of one or more sublingual phentermine spray compositions to "decrease" a relevant physiological or cellular response, such as a symptom of a disease like obesity or a condition like excessive weight described herein, as measured according to routine techniques in the diagnostic art. Relevant physiological or cellular responses (in vivo or in vitro) will be apparent to persons skilled in the art, and may include reductions in the symptoms or pathology of a disease such as obesity and related issues like inflammation or pain. A "decrease" in a response may be "statistically significant" as compared to the response produced by no sublingual phentermine spray composition or a control composition, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease, including all integers in between.

As used herein, the term "approximately" in reference to amounts refers to plus or minus 5% of the value given, such as wt. %. The term "about," a in reference to amounts refers to plus or minus 10% of the value given, such as wt. %.

General Embodiments

In various embodiments, a sublingual phentermine spray composition comprises phentermine or a phentermine salt, and a carrier, wherein the sublingual phentermine spray composition comprises a liquid having a viscosity of from about 1 cp to about 100 cp.

In various embodiments, the sublingual phentermine spray composition comprises from about 4.5 wt. % to about 10 wt. % phentermine-HCl, based on the total weight of the sublingual phentermine spray composition. In certain examples, a daytime use version of the sublingual phentermine spray composition comprises from about 7.5 wt. % up to about 10 wt. % phentermine-HCl, based on the total weight of the sublingual phentermine spray composition, whereas a nighttime version of the sublingual phentermine spray composition comprises from about 4.5 wt. % up to about 7.5 wt. % phentermine-HCl, based on the total weight of the sublingual phentermine spray composition. The lower amount of phentermine-HCl in the nighttime version lessens the insomnia otherwise caused by higher amounts of phentermine-HCl.

In various embodiments, the sublingual phentermine spray composition further comprises a sleep aid.

In various embodiments, a sublingual phentermine spray composition comprises phentermine or a phentermine salt, a sleep aid and a carrier, wherein the sublingual phentermine spray composition is a liquid having a viscosity of from about 1 cp to about 100 cp. In various embodiments, the sublingual phentermine spray composition comprises from about 4.5 wt. % to about 7.5 wt. % phentermine-HCl, and from about 0.75 wt. % to about 1.25 wt. % of the sleep aid, based on the total weight of the sublingual phentermine spray composition. The wt. % of the sleep aid depends upon the nature of the sleep aid (e.g., if the sleep aid is a drug active or an essential oil, for example). In various examples, the sleep aid is present at levels >1.25 wt. %, such as in an amount sufficient to promote sleep from sublingual dosing of the sublingual phentermine spray composition comprising a sleep aid.

In various examples, the carrier comprises an oil, such as fatty acid glycerides (mono-, di-, and/or triglycerides of small-, medium- or long-chain fatty acids).

In various examples, the carrier comprises an anionic, nonionic, cationic or amphoteric surfactant. In certain examples, the surfactant is a nonionic surfactant. In various examples, the surfactant comprises a polysorbate or sorbate ester.

In various examples, the carrier comprises a solvent. In certain examples, the solvent is any combination of small molecular weight alcohol or glycol (e.g., $<C_6$), preferably ethanol and/or propylene glycol.

In various examples, the carrier comprises a salt, such as sodium chloride or potassium chloride. In certain examples, the salt promotes transmucosal absorption and bioavailability, and/or adjusts viscosity, such as when used in combination with a surfactant, and/or a salt assists in adjusting a taste profile including masking of unpleasant tastes in the sublingual phentermine spray composition.

In various embodiments, a sublingual phentermine spray composition for daytime use in accordance with the present disclosure comprises phentermine or a phentermine salt and a carrier, wherein the sublingual phentermine spray composition is a liquid having a viscosity of from about 1 cp to about 100 cp.

In various embodiments, a sublingual phentermine spray composition for daytime use comprises phentermine-HCl in a carrier. In certain examples, a sublingual phentermine spray composition for daytime use comprises from about 7.5 wt. % to about 10.0 wt. % phentermine-HCl, based on the total weight of the sublingual phentermine spray composition for daytime use. In various embodiments, a sublingual phentermine spray composition for daytime use is formulated to provide about 7.5 mg active phentermine (base) per 0.12-0.14 mL dose of the composition.

In various embodiments, a sublingual phentermine spray composition for daytime use comprises phentermine-HCl in a carrier comprising an oil, a surfactant, a solvent, and optionally, a salt, a flavoring agent and/or sweetener and/or preservative.

In various embodiments, the oil comprises medium-chain triglycerides (MCT), present at from about 50 wt. % to about 75 wt. %, based on the total weight of the sublingual phentermine spray composition for daytime use. In certain examples, the MCT is preferably the major ingredient by weight.

In various embodiments, the surfactant comprises a nonionic surfactant comprising polysorbate 80 (e.g., Tween® 80), present at from about 8 wt. % to about 15 wt. %, based on the total weight of the sublingual phentermine spray composition for daytime use.

In various embodiments, the solvent is a low molecular weight alcohol or glycol, and in preferred examples is ethanol, present at from about 7.5 wt. % to about 10 wt. %, based on the total weight of the sublingual phentermine spray composition for daytime use.

In various embodiments, the sublingual phentermine spray composition for daytime use further comprises a salt, such as sodium chloride or potassium chloride, present at from about 0.5 wt. % to about 1.5 wt. %, based on the total weight of the sublingual phentermine spray composition for daytime use.

In various embodiments, the sublingual phentermine spray composition for daytime use further comprises any combination of flavoring agent, masking agent, and/or sweetener, with the combination present at from about 0.1 wt. % to about 15 wt. %, based on the total weight of the sublingual phentermine spray composition for daytime use, recognizing that these levels depend on the combination chosen, and the types of ingredients, to mask certain unpleasant tastes and to make the overall experience of sublingual administration acceptable to the user. In some instances, a combination of steviol glycosides at from about 0.6 wt. % to about 0.8 wt. %, flavoring agent such as peppermint oil at from about 0.1 wt. % to about 2 wt. %, and masking agent such as Bitter Stop™ at from about 0.1 wt. % to about 15 wt. % suffices to mask the unpleasant taste of the sublingual phentermine spray composition for daytime use and make the product overall acceptable to users in taste panels.

In various embodiments, a sublingual phentermine spray composition for nighttime use in accordance with the present disclosure comprises phentermine or a phentermine salt, a sleep aid, and a carrier, wherein the sublingual phentermine spray composition for nighttime use is a liquid having a viscosity of from about 1 cp to about 100 cp.

In various embodiments, a sublingual phentermine spray composition for nighttime use comprises phentermine-HCl and melatonin in a carrier.

In various embodiments, a sublingual phentermine spray composition for nighttime use comprises phentermine-HCl and melatonin in a carrier comprising an oil, a surfactant, a solvent, and optionally, a salt, a flavoring agent and/or sweetener and/or preservative.

In various embodiments, a sublingual phentermine spray composition for nighttime use comprises from about 4.5 wt. % to about 7.5 wt. % phentermine-HCl, based on the total weight of the sublingual phentermine spray composition for nighttime use. The lower amount of phentermine-HCl as compared to the daytime version helps mitigate the insomnia otherwise caused by higher amounts of phentermine, and this risk of insomnia is also mitigated by the presence of the sleep aid.

In various embodiments, the sleep aid comprises melatonin, present at from about 0.75 wt. % to about 1.25 wt. %, based on the total weight of the sublingual phentermine spray composition for nighttime use.

In various embodiments, a sublingual phentermine spray composition for nighttime use is formulated to provide about 5 mg active phentermine (base) and 1 mg melatonin per 0.12-0.14 mL dose of the composition.

In various embodiments, a sublingual phentermine spray composition for nighttime use comprises phentermine-HCl and a sleep aid in a carrier comprising an oil, a surfactant, a solvent, and optionally, a salt, a flavoring agent and/or sweetener and/or preservative.

In various embodiments, the oil comprises medium-chain triglycerides (MCT), present at from about 50 wt. % to about 75 wt. %, based on the total weight of the sublingual phentermine spray composition for nighttime use. In certain examples, the MCT is preferably the major ingredient by weight.

In various embodiments, the surfactant is a nonionic surfactant comprising polysorbate 80 (e.g., Tween® 80), present at from about 8 wt. % to about 15 wt. %, based on the total weight of the sublingual phentermine spray composition for nighttime use.

In various embodiments, the solvent is a low molecular weight alcohol or glycol, and in preferred examples is ethanol, present at from about 7.5 wt. % to about 10 wt. %, based on the total weight of the sublingual phentermine spray composition for nighttime use.

In various embodiments, the sublingual phentermine spray composition for nighttime use further comprises a salt, such as sodium chloride or potassium chloride, present at from about 0.5 wt. % to about 1.5 wt. %, based on the total weight of the sublingual phentermine spray composition for nighttime use.

In various embodiments, the sublingual phentermine spray composition for nighttime use further comprises any combination of flavoring agent, masking agent, and/or sweetener, with the combination present at from about 0.1 wt. % to about 15 wt. %, based on the total weight of the sublingual phentermine spray composition for nighttime use, recognizing that these levels depend on the combination chosen, and the types of ingredients, to mask certain unpleasant tastes and to make the overall experience of sublingual administration acceptable to the user. In some instances, a combination of steviol glycosides at from about 0.6 wt. % to about 0.8 wt. %, a flavoring agent such as peppermint oil at from about 0.1 wt. % to about 2 wt. %, and a masking agent such as Bitter Stop™ at from about 0.1 wt. % to about 15 wt. % suffices to mask the unpleasant taste of the sublingual phentermine spray composition for nighttime use and make the product acceptable to users.

In either daytime or nighttime sublingual phentermine spray compositions, sublingual phentermine spray compositions in accordance with the present disclosure preferably include at least a flavoring agent and a sweetener, and in more preferred examples, sublingual phentermine spray compositions include a combination of flavoring agent, such as peppermint oil, a masking agent, such as Bitter Stop™ available from PCCA, Houston, TX, and a non-sugar sweetener such as stevia, available as steviol glycerides from Cargill North America, Minneapolis, MN, or artificial sweetener such as aspartame, sucralose, acesulfame, or saccharin. In other examples, a sweetener for sublingual phentermine spray compositions may be a common sugar or sugar alcohol typically used in sweetening foods and medicines, such as sucrose, fructose, glucose, lactose, xylitol, mannitol, sorbitol, erythritol, and syrups therefrom, and so forth. Any of the natural and artificial sweeteners, alone or in combination, are used in the sublingual phentermine spray compositions at a total wt. % level sufficient to provide a consumer acceptable experience when using the sublingual phentermine spray composition.

In either daytime or nighttime compositions, sublingual phentermine spray compositions in accordance with the present disclosure may include a salt (e.g., sodium chloride, potassium chloride). In general, a salt is preferably included to increase solubility of phentermine or a phentermine salt in a carrier mixture and/or to increase viscosity in concert with a surfactant also present in the carrier. Other effects include, for example, increases in oral absorption of drugs such as phentermine. Yet another reason for the inclusion of salt in the sublingual phentermine spray compositions of the present disclosure is for taste masking. For a review of these concepts, see H. Sohi, "Taste Masking Technologies in Oral Pharmaceuticals: Recent Developments and Approaches." *Drug Development and Industrial Pharmacy*, 30(5), 429-448 (2004).

Table 1 sets forth these three embodiments (I-general, II-daytime version, III-nighttime version) of sublingual phentermine spray compositions in accordance with the present disclosure. The compositions are in the physical form of a thin liquid (i.e., a liquid having viscosity less than 100 cp, preferably less than 50 cp, and more preferably less than about 20 cp), which can be filled into small non-aerosol throat/mouth spray bottles that can be actuated to provide a bolus or a spray dosage for transmucosal (particularly, sublingual) administration, and preferably from about 0.10 to about 0.20 mL per actuation.

TABLE 1

Sublingual Phentermine Spray Compositions

| Ingredient (wt. %) | I (General) | II (Daytime) | III (Nighttime) |
|---|---|---|---|
| Phentermine-HCl | 4.5 to 10 | 7.5 to 10 | 4.5 to 7.5 |
| Sleep Aid | 0 to 1.25 | -0- | 0.75 to 1.25 |
| Oil | 50 to 75 | 50 to 75 | 50 to 75 |
| Surfactant | 8 to 15 | 8 to 15 | 8 to 15 |
| Solvent | 7.5 to 10 | 7.5 to 10 | 7.5 to 10 |
| Salt | 0.5 to 1.5 | 0.5 to 1.5 | 0.5 to 1.5 |
| Flavoring, masking agent, and/or sweetener | 0.1 to 15 | 0.1 to 15 | 0.1 to 15 |
| | | | |
| Total | 100.00 wt. % | 100.00 wt. % | 100.00 wt. % |
| Physical Appearance | Liquid | Liquid | Liquid |
| Transmucosal route of administration | Sublingual | Sublingual | Sublingual |
| Recommended dosage (spray volume) | 0.12-0.14 mL | 0.12-0.14 mL | 0.12-0.14 mL |
| Preferred active phentermine per 0.12 mL dose | 7.5 mg | 7.5 mg | 5 mg |
| Recommended sleep aid per 0.12 mL dose | 0 to 1 mg | -0- | 1 mg |

As mentioned, sublingual phentermine spray compositions in accordance with the present disclosure may comprise any combination of optional excipients, such as flavoring agents, masking agents, sweeteners, and/or preservatives. In various embodiments, sublingual phentermine spray compositions contain no excipients.

In various embodiments, the optional one or more excipients include any one or combination of flavoring agent, sweetener, buffer (or acidic agent and/or alkali agent), colorant, transmucosal permeation enhancer, stabilizer, preservative, or other pharmaceutically acceptable substance. Any of these materials not specifically mentioned herein may be found in "Handbook of Pharmaceutical Excipients, 6$^{th}$ Edition, R. C Rowe, et al., editors, Pharmaceutical Press, London, 2009.

Suitable flavoring agents can include, for example, flavors, such as, natural flavors, artificial flavors, and combinations thereof. Non-limiting examples of flavor oils include spearmint oil, cinnamon oil, oil of wintergreen (methyl salicylate), peppermint oil, clove oil, bay oil, anise oil, eucalyptus oil, thyme oil, cedar leaf oil, oil of nutmeg, allspice, oil of sage, mace, oil of bitter almonds, and cassia oil. Suitable flavoring agents also include, for example, artificial, natural and synthetic fruit flavors such as vanilla, citrus oils (e.g., lemon, orange, lime, and grapefruit), and fruit essences (e.g., apple, pear, peach, grape, strawberry, raspberry, cherry, plum, pineapple, and apricot), and the like, and combinations thereof. Depending on the sleep aid used in the nighttime versions of sublingual phentermine spray compositions, these flavoring agents can be used alone or in various combinations, and certain combinations may provide better results than peppermint oil.

Other flavoring agents and fragrant aromatics that may be included individually or in combination include, but are not limited to, anethole, menthol, menthone, menthyl acetate, eucalyptol, borneol, borneol acetate, camphor, 1,8-cineole, cinnamaldehyde, benzaldehyde, citral, thujone, eugenol, limonene, geraniol, citronellol, citronellal, pinene, linalool, thymol, carvone, caryophyllene, linalyl acetate, methyl salicylate, and mixtures thereof. Also, substances that provide scent and flavor include, but are not limited to, 3,3,5-trimethylcyclohexanol, methoxycyclohexanol, benzyl alcohol, anise alcohol, cinnamyl alcohol, β-phenyl ethyl alcohol (2-phenylethanol), cis-3-hexenol, musk xylol, isoeugenol, methyl eugenol, α-amylcinnamic aldehyde, anisaldehyde, n-butyl aldehyde, cumin aldehyde, cyclamen aldehyde, decanal, isobutyl aldehyde, hexyl aldehyde, heptyl aldehyde, n-nonyl aldehyde, nonadienol, hydroxycitronellal, benzaldehyde, methyl nonyl acetaldehyde, dodecanol, α-hexylcinnamic aldehyde, undecenal, heliotropin, vanillin, ethyl vanillin, methyl amyl ketone, methyl β-naphthyl ketone, methyl nonyl ketone, musk ketone, diacetyl, acetyl propionyl, acetyl butyryl, acetophenone, p-methyl acetophenone, ionone, methyl ionone, amyl butyrolactone, diphenyl oxide, methyl phenyl glycidate, γ-nonyl lactone, coumarin, cineole, ethyl methyl phenyl glycidate, methyl formate, isopropyl formate, linalyl formate, ethyl acetate, octyl acetate, methyl acetate, benzyl acetate, butyl propionate, isoamyl acetate, isopropyl isobutyrate, geranyl isovalerate, allyl caproate, butyl heptylate, octyl caprylate octyl, methyl heptanecarboxylate, methine octanecarboxylate, isoacyl caprylate, methyl laurate, ethyl myristate, methyl myristate, ethyl benzoate, benzyl benzoate, methylcarbomoylphenyl acetate, isobutyl phenylacetate, methyl cinnamate, cinnamyl cinnamate, ethyl anisate, methyl anthranilate, ethyl pyruvate, ethyl α-butyl butylate, benzyl propionate, butyl acetate, butyl butyrate, p-tert-butylcyclohexyl acetate, cedryl acetate, citronellyl acetate, citronellyl formate, p-cresyl acetate, ethyl butyrate, ethyl caproate, ethyl cinnamate, ethyl phenylacetate, ethylene brassylate, geranyl acetate, geranyl formate, isoamyl salicylate, isoamyl isovalerate, isobornyl acetate, linalyl acetate, methyl anthranilate, methyl dihydrojasmonate, β-phenylethyl acetate, trichloromethylphenyl carbinyl acetate, terpinyl acetate, vetiveryl acetate, and mixtures thereof. Some of these compounds are going to function as masking agents, and there is no attempt here to distinguish from what might purely be a flavoring agent and what might purely be a masking agent since a masking agent is likely to have some flavor profile.

Suitable sweeteners include nutritive carbohydrates such as sucrose, glucose, fructose, trehalose, galactose, mannitol, sorbitol, xylitol, and the like, artificial sweeteners such as saccharin, aspartame, acesulfame K, cyclamates, neotame, sucralose, and neohesperidin dihydrochalcone (NHDC) and the like, and the naturally obtainable, non-sugar sweetener, stevia (i.e., steviol glycosides obtained from the plant species, *Stevia rebaudiana*.

Suitable buffers may comprise one or more acidifying agents or alkaline agents as necessary to neutralize various co-ingredients, form salts of various co-ingredients, and/or achieve a particular pH target for the composition, such as to adjust the local environment in the oral cavity. Combinations of various acidifying agents and alkaline agents may be used to create buffering systems that stabilize the desired final pH of the composition. Buffers may be mixed buffers, meaning that the alkaline agent is not necessarily the conjugate base of the acidifying agent.

Exemplary acidifying agents for use in the present compositions include, but are not limited to, organic acids of any molecular weight and mineral acids (inorganic acids such as HCl), and mixtures thereof. Organic acids may include mono-carboxylic acids, di-carboxylic acids, or tri-carboxylic acids, and may be saturated or may have any degree of unsaturation. For example, organic acids for use in various embodiments of the composition in accordance to the present disclosure may include, but are not limited to, formic acid, carbonic acid, acetic acid, lactic acid, oxalic acid, propionic acid, valeric acid, enanthic acid, pelargonic acid, butyric acid, lauric acid, docosahexaenoic acid, eicosapentaenoic acid, pyruvic acid, acetoacetic acid, benzoic acid, salicylic acid, aldaric acid, fumaric acid, glutaconic acid, traumatic acid, muconic acid, malonic acid, malic acid, succinic acid, glutaric acid, adipic acid, pimelic acid, suberic acid, azelaic acid, abietic acid, pimaric acid, sebacic acid, phthalic acid, isophthalic acid, terephthalic acid, maleic acid, citric acid, and combinations thereof. Any one or combination of these acids may be used to protonate phentermine in situ to convert it to a phentermine salt. Stated another way, a sublingual phentermine spray composition may be compounded with phentermine (the free base), and then a suitable acid such as hydrochloric acid added to the mixture, which is then assumed to contain phentermine-HCl.

Exemplary alkaline materials include any organic amines, $NH_3$, alkali metal or alkaline earth hydroxide, any conjugate bases of any organic acids (e.g. R—COO$^-$), and any of the salts of carbonic acid, phosphoric acid, nitric acid and sulfuric acid, and any mixtures thereof. For example, alkaline materials for use in various embodiments of the composition in accordance with the present disclosure may include, but are not limited to, NaOH, KOH, $NH_3$, sodium acetate, sodium succinate, disodium succinate, monosodium citrate, disodium citrate, trisodium citrate, $NaH_2PO_4$, $Na_2HPO_4$, $Na_3PO_4$, $KH_2PO_4$, $K_2HPO_4$, $K_3PO_4$, $NaHSO_4$, $Na_2SO_4$, $KHSO_4$, $K_2SO_4$, $NaHCO_3$, $Na_2CO_3$, $KHCO_3$, $K_2CO_3$, $NaH_3P_2O_7$, $Na_2H_2P_2O_7$, $Na_3HP_2O_7$, $Na_4P_2O_7$, $KH_3P_2O_7$, $K_2H_2P_2O_7$, $K_3HP_2O_7$, $K_4P_2O_7$, and mixtures thereof. Any of these chemical species may exist as various hydrates when purchased as raw materials for use in the present compositions.

Exemplary colorants include the pharmaceutically acceptable colors used in liquid pharmaceutical dosage forms, such as the United States Food & Drug Administration (FDA) certified colors for use in pharmaceutical compositions. These acceptable colorants include the water soluble colors D&C Green 8, Yellow 10, Yellow 8, Orange 4, Red 22, Red 28, Red 33, Green 5, quinoline yellow, FD&C Yellow 5, Yellow 6, Red 4, Red 40, Red 3, Green 3, Blue 1, and Blue 2. These colorants, if even used in the liquid compositions, are simply for aesthetic reasons, and might be desirable if transparent throat/mouth spray bottles are used to contain and dispense the sublingual phentermine spray compositions.

In various embodiments, sublingual phentermine spray compositions in accordance with the present disclosure may also include a transmucosal permeation enhancer to accelerate absorption of the phentermine or phentermine salt sublingually. Suitable transmucosal permeation enhancers include, but are not limited to, surfactants that assist bioabsorption, including, for example, fatty acids and/or esters or salts thereof, bile acids and/or salts thereof. In some instances, a permeation enhancer may be a polysorbate or sorbate ester but having a different POE level than polysorbate 80 used in various preferred examples as oil carrier (e.g., polysorbate 20). For a review of transmucosal permeation enhancers that find use herein, see B. Aungst, "Comparison of the effects of various transmucosal absorption promoters on buccal insulin delivery," *International Journal of Pharmaceutics*, 53(3), 227-235 (1989).

Stabilizers and preservatives for oral compositions include the parabens, sorbitol, sodium benzoate, benzoic acid, sorbic acid, potassium sorbate, propionic acid, and combinations thereof. In some instances, ethanol might be present at levels sufficient to mitigate bacterial growth in the compositions. Antioxidants include, but are not limited to, Vitamin C, Vitamin E, butylated hydroxyanisole (BHA), butylated hydroxytoluene (BHT), and propylgallate. For a review see, I. Himoudy, "Preservatives and their role in pharma and clinical research," *International Journal of Pharma Sciences and Scientific Research*, 2:4, 134-151 (2016).

Exemplary Compositions, Dosage Forms, and Methods of Administration

Table 2 sets forth two exemplary sublingual phentermine spray compositions in accordance with the present disclosure, Composition 1 being a preferred composition for daytime use, and Composition 2 being a preferred composition for nighttime use. Each of these compositions are obtained by simple mixing of ingredients with some heating as necessary, as detailed below. Each of the two exemplary composition in Table 2 appear as thin liquids and each are filled into a 2 mL to 60 mL throat/mouth spray bottle, or other suitable non-aerosol dispenser, preferably less than about 30 mL (1 fluid ounce) or more preferably less than about 10 mL (0.33 fluid ounce) in volume, such as from ULINE or U.S. Plastics Corporation, equipped with a non-aerosol pump actuator capable of dispensing about 0.10 mL to about 0.20 mL per actuation, preferably about 0.12-0.14 mL per actuation. A throat sprayer usually includes an extension wand fluidically attached to the actuator, and this wand is convenient for sublingual administration as the liquid dose can be directed precisely to a location under the tongue. The actuator can be chosen for bolus or spray droplets, and in some instances an aerosolizing nozzle can be configured at the end of an extension wand.

TABLE 2

Exemplary Sublingual Phentermine Spray Compositions and Dosages:

|  | Composition | |
| --- | --- | --- |
| Ingredients (in wt. %) | 1 | 2 |
| Phentermine-HCl | 8.2 | 5.5 |
| Melatonin | 0 | 0.9 |
| Medium-chain triglyceride (MCT) | 59.2 | 60.9 |

TABLE 2-continued

Exemplary Sublingual Phentermine Spray Compositions and Dosages:

| Ingredients (in wt. %) | Composition 1 | Composition 2 |
| --- | --- | --- |
| Polysorbate 80 | 11.2 | 11.3 |
| Ethanol | 8.3 | 8.3 |
| Sodium chloride | 1.0 | 1.0 |
| Peppermint oil and steviol glycosides (presented in total) | 1.6 | 1.6 |
| Masking agent (e.g., Bitter Stop ™)[1] | 10.5 | 10.5 |
| Total | 100.0 | 100.0 |
| Wt. % active phentermine[2] based on total wt. of composition | 6.6 | 4.4 |
| Recommended dose volume per non-aerosol pump actuation | 0.12-0.14 mL | 0.12-0.14 mL |
| Active phentermine (free base) per dose volume | 7.5-8.7 mg | 5.0-5.8 mg |
| Melatonin per dose volume | 0 | 1-1.2 |

Table 2 Notes:

(1) The amount of masking agent used is going to vary based on the selection of masking agent, the recommended use level instructed by the supplier, and an empirical optimization obtained from, for example, taste panels with consumers. Less solvent diluted masking agents, or powdered substances, can be used at notably lesser amounts than 10.5 wt. %. In general embodiments, a masking agent may be eliminated entirely, such as when a single flavoring agent or combination of flavoring agents and sweetener suffice to provide a consumer acceptable experience.

(2) Phentermine (free base) has a molecular weight of 149.23 whereas phentermine-HCl has a molecular weight of 185.69. Hence, 80.4 wt. % of phentermine-HCl is active phentermine. Stated more simply, 1 mg phentermine-HCl provides 0.804 mg active phentermine. This conversion is taken into consideration when calculating active phentermine provided from doses of liquid compositions comprising phentermine-HCl, in further consideration that the specific gravity of the sublingual phentermine spray compositions herein is <1 g/mL (such as, for example, an average of about 0.95 g/mL).

The compositions of Tables 1 and 2 are produced by simple mixing in accordance with the following procedure:

All solid ingredients are first triturated together to reduce overall particle size. This powder mixture is then added to a vessel containing both the oil and the solvent. The resulting mixture is mixed under gentle heating to wet and partially dissolve the solids. The flavoring agents and sweetener are added, followed by the surfactant, and the mixture continually stirred until complete dissolution is achieved. If necessary, additional oil is added to reach a final target volume.

Dosage Regimens and Dosage Amounts

In various embodiments, methods for (a) suppressing appetite in an individual in need thereof, (b) losing weight in obese and/or overweight individuals in need thereof, such as those clinically diagnosed as obese, and (c) maintaining a healthy weight or desired appearance in an individual in need thereof, are described.

In various embodiments, an individual in need thereof has been diagnosed as overweight or obese, as per ICD-10 code E66 and subgroups. This diagnosis is discussed in S. B. Gribsholt, et al., "Validity of ICD-10 diagnoses of overweight and obesity in Danish hospitals." *Clin. Epidemiol.,* 11, 845-854 (2019). These individuals in need thereof may seek therapeutic treatments of their obesity with a weight loss regimen comprising sublingual phentermine spray compositions in accordance with the present disclosure.

In various embodiments, a method for suppressing appetite in an individual in need thereof comprises sublingually administering to the individual a therapeutically effective amount of a sublingual phentermine spray composition. In various examples, the individual in need thereof is clinically diagnosed as overweight or obese. In various embodiments, the therapeutically effective amount of the sublingual phentermine spray composition comprises an amount sufficient to sublingually provide from about 7.5 mg to about 37.5 mg of active phentermine daily. This daily regimen is continued for a time necessary to obtain a desired outcome. In various examples, the sublingual phentermine spray composition in the regimen comprises from about 4.5 wt. % to about 10 wt. % phentermine-HCl.

In various embodiments, a method for suppressing appetite in an individual in need thereof comprises sublingually administering to the individual a therapeutically effective amount of both (i.e., in combination) a sublingual phentermine spray composition for daytime use and a sublingual phentermine spray composition for nighttime use. In various examples, the individual in need thereof is clinically diagnosed as overweight or obese. In various embodiments, the therapeutically effective amount of the sublingual phentermine spray composition for daytime use and a sublingual phentermine spray composition for nighttime use comprises an amount sufficient of both combined to sublingually provide from about 12.5 mg to about 37.5 mg of active phentermine daily and from about 1 mg to about 3 mg of a sleep aid daily. In various examples, the sublingual phentermine spray composition for daytime use is administered in a single or multiple doses at once during the day, and the sublingual phentermine spray composition for nighttime use is administered in a single or multiple doses at once in the evening, such as within an hour before bedtime. This daily regimen is continued for a time necessary to obtain a desired outcome. In various examples, the sublingual phentermine spray composition for daytime use comprises from about 7.5 wt. % to about 10 wt. % phentermine-HCl and the sublingual phentermine spray composition for nighttime use comprises from about 4.5 wt. % to about 7.5 wt. % phentermine-HCl and from about 0.75 wt. % to about 1.25 wt. % of melatonin. In various embodiments, both the sublingual phentermine spray composition for daytime use and the sublingual phentermine spray composition for nighttime use are provided in small non-aerosol spray bottles in a package together as a kit with use instructions on package labeling, on an insert within the package, or online on a website.

In various embodiments, a method of losing weight in an individual in need thereof comprises sublingually administering to the individual a therapeutically effective amount of a sublingual phentermine spray composition. In various examples, the individual in need thereof is clinically diagnosed as overweight or obese. In various embodiments, the therapeutically effective amount of the sublingual phentermine spray composition comprises an amount sufficient to sublingually provide from about 7.5 mg to about 37.5 mg of active phentermine daily. This daily regimen is continued for a time necessary to obtain a desired outcome. In various examples, the sublingual phentermine spray composition in the regimen comprises from about 4.5 wt. % to about 10 wt. % phentermine-HCl.

In various embodiments, a method promoting weight loss in an individual in need thereof comprises sublingually administering to the individual a therapeutically effective amount of both a sublingual phentermine spray composition for daytime use and a sublingual phentermine spray composition for nighttime use. In various examples, the individual in need thereof is clinically diagnosed as overweight or obese. In various embodiments, the therapeutically effective amount of the sublingual phentermine spray composition for daytime use and a sublingual phentermine spray composition for nighttime use comprises an amount sufficient of both combined to sublingually provide from about 12.5 mg to about 37.5 mg of active phentermine daily and from about 1 mg to about 3 mg of a sleep aid daily. In various examples, the sublingual phentermine spray composition for daytime use is administered in a single or multiple doses at once during the day, and the sublingual phentermine spray composition for nighttime use is administered in a single or multiple doses at once in the evening, such as within an hour before bedtime. This daily regimen is continued for a time necessary to obtain a desired outcome. In various examples, the sublingual phentermine spray composition for daytime use comprises from about 7.5 wt. % to about 10 wt. % phentermine-HCl and the sublingual phentermine spray composition for nighttime use comprises from about 4.5 wt. % to about 7.5 wt. % phentermine-HCl and from about 0.75 wt. % to about 1.25 wt. % of melatonin. In various embodiments, both the sublingual phentermine spray composition for daytime use and the sublingual phentermine spray composition for nighttime use are provided in small non-aerosol spray bottles in a package together as a kit with use instructions on package labeling, on an insert within the package, or online on a website.

In various embodiments, a method for maintaining overall health, weight or BMI or for maintaining an overall healthy appearance in an individual in need thereof comprises sublingually administering to the individual a prophylactically effective amount of a sublingual phentermine spray composition. In various examples, the individual in need thereof is not clinically diagnosed as overweight or obese, but instead desires maintenance of a certain physical appearance or overall healthy state. In various embodiments, the prophylactically effective amount of the sublingual phentermine spray composition comprises an amount sufficient to sublingually provide from about 7.5 mg to about 37.5 mg of active phentermine daily. This daily regimen is continued for a time necessary to obtain a desired outcome, which in the case of maintaining overall health and weight might be indefinitely, i.e., throughout the life of the individual. In various examples, the sublingual phentermine spray composition in the regimen comprises from about 4.5 wt. % to about 10 wt. % phentermine-HCl.

In various embodiments, a method for maintaining overall health, weight or BMI or for maintaining an overall healthy appearance in an individual in need thereof comprises sublingually administering to the individual a prophylactically effective amount of both a sublingual phentermine spray composition for daytime use and a sublingual phentermine spray composition for nighttime use. In various examples, the individual in need thereof is not clinically diagnosed as overweight or obese, but instead desires maintenance of a certain physical appearance or overall healthy state. In various embodiments, the prophylactically effective amount of the sublingual phentermine spray composition for daytime use and a sublingual phentermine spray composition for nighttime use comprises an amount sufficient of both combined to sublingually provide from about 12.5 mg to about 37.5 mg of active phentermine daily and from about 1 mg to about 3 mg of a sleep aid daily. In various examples, the sublingual phentermine spray composition for daytime use is administered in a single or multiple doses at once during the day, and the sublingual phentermine spray composition for nighttime use is administered in a single or multiple doses at once in the evening, such as within an hour before bedtime. This daily regimen is continued for a time necessary to obtain a desired outcome, which in the case of maintaining overall health and weight might be indefinitely, i.e., throughout the life of the individual. In various examples, the sublingual phentermine spray composition for daytime use comprises from about 7.5 wt. % to about 10 wt. % phentermine-HCl and the sublingual phentermine spray composition for nighttime use comprises from about 4.5 wt. % to about 7.5 wt. % phentermine-HCl and from about 0.75 wt. % to about 1.25 wt. % of melatonin. In various embodiments, both the sublingual phentermine spray composition for daytime use and the sublingual phentermine spray composition for nighttime use are provided in small non-aerosol spray bottles in a package together as a kit with use instructions on package labeling, on an insert within the package, or online on a website.

A dose of a sublingual phentermine spray composition herein is from about 0.10 mL to about 0.20 mL, preferably from about 0.12 to about 0.14 mL, with a single dose preferably comprising a single actuation of a pump actuator on a non-aerosol spray bottle. A single 0.12 mL dose of a sublingual phentermine spray composition preferably provides about 7.5 mg active phentermine (free base). Thus, three (3) 0.12 mL doses of a sublingual phentermine spray composition preferably provides a total of about 22.5 mg active phentermine.

A dose of a sublingual phentermine spray composition for daytime use is from about 0.10 mL to about 0.20 mL, preferably from about 0.12 to about 0.14 mL, with a single dose preferably comprising a single actuation of a pump actuator on a non-aerosol spray bottle. A single 0.12 mL dose of a sublingual phentermine spray composition for daytime use preferably provides about 7.5 mg active phentermine (free base). Thus, three (3) 0.12 mL doses of a sublingual phentermine spray composition for daytime use preferably provides a total of about 22.5 mg active phentermine.

A dose of a sublingual phentermine spray composition for nighttime use also has a volume of from about 0.10 mL to about 0.20 mL, preferably from about 0.12 to about 0.14 mL, with a single dose preferably comprising a single actuation of a pump actuator on a non-aerosol spray bottle. A single 0.12 mL dose of a sublingual phentermine spray composition for nighttime use preferably provides about 5 mg active phentermine (free base) and about 1 mg melatonin. Thus, three (3) 0.12 mL doses of a sublingual phentermine spray composition for nighttime use preferably provides a total of about 15 mg active phentermine and about 3 mg melatonin. If another sleep aid is used instead of melatonin in the nighttime composition, the amount of active sleep aid per dose might vary considerably from this amount, and the preferred amount may be in line with a prescribed drug active to induce sleep.

The single spray dose or multiple spray doses of sublingual phentermine spray composition for daytime use can be taken throughout the waking day, although in preferred methods, multiple doses, such as 3×0.12 mL can be administered sublingually in rapid succession, for example, at one time in the morning. The single spray dose or multiple spray doses of sublingual phentermine spray composition for nighttime use should be taken close to bedtime in view of the presence of a sleep aid in the composition. Therefore, multiple doses, such as 3×0.12 mL can be administered sublingually in rapid succession, for example just prior to bedtime. When melatonin is the sleep aid in the nighttime composition, timing is generally per the recommendations for using melatonin.

In various embodiments, methods for (a) suppressing appetite in an individual in need thereof, (b) losing weight in obese and overweight individuals in need thereof, such as those clinically diagnosed as obese, and (c) maintaining a healthy weight or desired appearance in an individual in need thereof, comprise use of both a daytime version and a nighttime version of a sublingual phentermine spray composition. With the above mentioned dosing and regimens, it should be noted that in preferred embodiments, 3×0.12 mL of daytime composition and 3×0.12 mL nighttime composition, both used daily, provide 37.5 mg active phentermine daily, which coincides with the single dose 37.5 mg oral phentermine tablet for oral ingestion, except without the side effects such as daytime drowsiness and intestinal discomfort, and without the nighttime insomnia.

Kits

In various embodiments, a kit for (a) suppressing appetite in an individual in need thereof, (b) losing weight in obese and overweight individuals in need thereof, and (c) maintaining a healthy weight or desired appearance in an individual in need thereof, comprises a sublingual phentermine spray composition for daytime use; a sublingual phentermine spray composition for nighttime use; a package that provides both; and suitable information for the use of the two compositions.

In various embodiments, a kit for suppressing appetite in an individual in need thereof comprises a first non-aerosol pump spray bottle containing a sublingual phentermine spray composition for daytime use, the sublingual phentermine spray composition for daytime use comprising phentermine or a phentermine salt in a carrier; a second non-aerosol pump spray bottle containing a sublingual phentermine spray composition for nighttime use, the sublingual phentermine spray composition for nighttime use comprising phentermine or a phentermine salt and a sleep aid in a carrier; packaging to suitably hold both first and second non-aerosol spray bottles; and labeling on or in the package, or a website that provides instructions for use of the compositions in a regimen for suppressing appetite.

In various embodiments, a kit for losing weight in obese and/or overweight individuals in need thereof comprises a first non-aerosol pump spray bottle containing a sublingual phentermine spray composition for daytime use, the sublingual phentermine spray composition for daytime use comprising phentermine or a phentermine salt in a carrier; a second non-aerosol pump spray bottle containing a sublingual phentermine spray composition for nighttime use, the sublingual phentermine spray composition for nighttime use comprising phentermine or a phentermine salt and a sleep aid in a carrier; packaging to suitably hold both first and second non-aerosol spray bottles; and labeling on or in the package, or a website that provides instructions for use of the compositions in a regimen for losing weight.

In various embodiments, a kit for maintaining a healthy weight or desired appearance in an individual in need thereof comprises a first non-aerosol pump spray bottle containing a sublingual phentermine spray composition for daytime use, the sublingual phentermine spray composition for daytime use comprising phentermine or a phentermine salt in a carrier; a second non-aerosol pump spray bottle containing a sublingual phentermine spray composition for nighttime use, the sublingual phentermine spray composition for nighttime use comprising phentermine or a phentermine salt and a sleep aid in a carrier; packaging to suitably hold both first and second non-aerosol spray bottles; and labeling on or in the package, or a website that provides instructions for use of the compositions in a regimen for maintaining a healthy weight or a desired appearance.

In various embodiments, the daytime and nighttime compositions in the various kits comprise phentermine-HCl. In preferred examples, the nighttime compositions comprise phentermine-HCl and melatonin.

In preferred embodiments, the first and second non-aerosol pump spray bottles are about 10 mL in volume, such as to align with a medical prescription. In certain examples, a single actuation of either the first or second non-aerosol pump spray bottles dispenses about 0.12 to 0.14 mL, and in some examples, a bottle containing 10 mL of daytime or nighttime composition will provide for about eighty three (83) 0.12 mL spray doses.

In various embodiments, a kit may include a web address instead of paper instructions directing the user to a website that provides detailed use instructions for the kit, including dosage regimens, expectations, and the like. In other examples, a kit may comprise labeling on the package, such as printed instructions on a carton, or a pamphlet or other written instructions suitably sized and optionally folded up inside the package.

In various embodiments, the packaging comprises a cardboard carton or a plastic tray with a card backing, or a plastic clamshell.

Sublingual phentermine spray compositions, methods of use thereof, and kits comprising same are provided. In the detailed description herein, references to "various embodiments", "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Benefits, other advantages, and solutions to problems have been described herein with regard to specific embodiments. However, the benefits, advantages, solutions to problems, and any elements that may cause any benefit, advantage, or solution to occur or become more pronounced are not to be construed as critical, required, or essential features or elements of the disclosure. The scope of the disclosure is accordingly to be limited by nothing other than the appended claims, in which reference to an element in the singular is not intended to mean "one and only one" unless explicitly so stated, but rather "one or more." Moreover, where a phrase similar to 'at least one of A, B, and C' or 'at least one of A, B, or C' is used in the claims or specification, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C.

All structural, chemical, and functional equivalents to the elements of the above-described various embodiments that are known to those of ordinary skill in the art are expressly incorporated herein by reference and are intended to be encompassed by the present claims. Moreover, it is not necessary for a composition or method to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims. No claim element is intended to invoke 35 U.S.C. 112(f) unless the element is expressly recited using the phrase "means for." As used herein, the terms "comprises," "comprising." or any other variation thereof, are intended to cover a non-exclusive inclusion, such that a chemical, chemical composition, process, method, article, or apparatus that comprises a list of elements does not include only those elements but may include other elements not expressly listed or inherent to such chemical, chemical composition, process, method, article, or apparatus.

The invention claimed is:

1. A method for suppressing appetite or for promoting weight loss in an individual in need thereof, the method comprising:

sublingually administering to the individual a therapeutically effective amount of a combination of a sublingual phentermine spray composition for daytime use and a sublingual phentermine spray composition for nighttime use;

wherein the sublingual phentermine spray composition for daytime use comprises from about 7.5 wt. % to about 10 wt. % phentermine-HCl, based on the total weight of the sublingual phentermine spray composition for daytime use; a solvent comprising ethanol, wherein the ethanol is present at from about 7.5 wt. % to about 10 wt. %, based on the total weight of the sublingual phentermine spray composition for daytime use; polysorbate 80, wherein the polysorbate 80 is present at from about 8 wt. % to about 15 wt. % 7, based on the total weight of the sublingual phentermine spray composition for daytime use; and a carrier comprising medium-chain triglycerides (MCT), wherein the MCT is present at from about 50 wt. % to about 75 wt. %, based on the total weight of the sublingual phentermine spray composition for daytime use;

wherein the sublingual phentermine spray composition for nighttime use comprises from about 4.5 wt. % to about 7.5 wt. % phentermine-HCl, based on the total weight of the sublingual phentermine spray composition for nighttime use; from about 0.75 wt. % to about 1.25 wt. % of a sleep aid, based on the total weight of the sublingual phentermine spray composition for nighttime use; a solvent comprising ethanol, wherein the ethanol is present at from about 7.5 wt. % to about 10 wt. %, based on the total weight of the sublingual phentermine spray composition for nighttime use; polysorbate 80, wherein the polysorbate 80 is present at from about 8 wt. % to about 15 wt. %, based on the total weight of the sublingual phentermine spray composition for nighttime use; and a carrier comprising medium-chain triglycerides (MCT), wherein the MCT is present at from about 50 wt. % to about 75 wt. %, based on the total weight of the sublingual phentermine spray composition for nighttime use;

wherein each of the sublingual phentermine spray composition for daytime use and the sublingual phentermine spray composition for nighttime use is a liquid having a viscosity of from about 1 cp to about 100 cp; and wherein the sublingual phentermine spray composition for daytime use is sublingually administered to the individual in the daytime hours and wherein the sublingual phentermine spray composition for nighttime use is sublingually administered to the individual at night before bedtime.

2. The method of claim 1, wherein the sleep aid is melatonin.

3. The method of claim 2, wherein the therapeutically effective amount is an amount sufficient of the combination of sublingual phentermine spray composition for daytime use and the sublingual phentermine spray composition for nighttime use to deliver a total of from about 12.5 mg to about 37.5 mg active phentermine and from about 1 mg to about 3 mg melatonin daily.

4. The method of claim 3, wherein the total of from about 12.5 mg to about 37.5 mg active phentermine and from about 1 mg to about 3 mg melatonin daily is obtained from one to three spray doses daily of the sublingual phentermine spray composition for daytime use and from one to three spray doses daily of the sublingual phentermine spray composition for nighttime use.

5. The method of claim 1, wherein the individual in need thereof is diagnosed overweight or obese.

6. The method of claim 1, wherein an amount of phentermine (free base) per 0.12 ml of the sublingual phentermine spray composition for daytime use is 7.5 mg.

7. The method of claim 2, wherein an amount of phentermine (free base) per 0.12 ml of the sublingual phentermine spray composition for nighttime use is 5 mg.

\* \* \* \* \*